(12) United States Patent
Machover et al.

(10) Patent No.: US 9,051,562 B2
(45) Date of Patent: Jun. 9, 2015

(54) **POLYPEPTIDES ISOLATED FROM *BREVIBACTERIUM AURANTIACUM* AND THEIR USE FOR THE TREATMENT OF CANCER**

(75) Inventors: David Machover, Villejuif (FR); Pascal Bonnarme, Thiverval-grignon (FR)

(73) Assignees: Institut National de la Santé et de la Recherche Médicale (INSERM), Paris (FR); INRA (Institut National de la Recherche Agronomique), Paris Cedex (FR); UNIVERSITE PARIS SUD-PARIS XI, Orsay Cedex (FR)

( * ) Notice: Subject to any disclaimer, the term of this patent is extended or adjusted under 35 U.S.C. 154(b) by 0 days.

(21) Appl. No.: 14/126,253

(22) PCT Filed: Jun. 15, 2012

(86) PCT No.: PCT/EP2012/061497
§ 371 (c)(1),
(2), (4) Date: Feb. 4, 2014

(87) PCT Pub. No.: WO2012/172074
PCT Pub. Date: Dec. 20, 2012

(65) Prior Publication Data
US 2014/0140978 A1    May 22, 2014

Related U.S. Application Data

(60) Provisional application No. 61/504,363, filed on Jul. 5, 2011.

(30) Foreign Application Priority Data

Jun. 15, 2011   (EP) ..................................... 11305748

(51) Int. Cl.
*C07K 14/345*    (2006.01)
*A61K 38/00*     (2006.01)
*C12N 9/88*      (2006.01)
*C12N 9/14*      (2006.01)
*C07K 14/435*    (2006.01)

(52) U.S. Cl.
CPC ................ *C12N 9/88* (2013.01); *C07K 14/345* (2013.01); *C12Y 303/01001* (2013.01); *C12N 9/14* (2013.01); *C12Y 404/01011* (2013.01); *A61K 38/00* (2013.01); *C07K 14/435* (2013.01)

(58) Field of Classification Search
CPC ............................... C07K 14/354; A61K 38/00
See application file for complete search history.

(56) References Cited

FOREIGN PATENT DOCUMENTS

WO           00/29589 A1    5/2000

OTHER PUBLICATIONS

El-Sayed, 2010, Microbial L-methioninase: production, molecular characterization, and therapeutic applications, Appl. Microbiol. Biotechnol. 86: 445-467.*
Sato et al., 2009, Methionine Gamma-Lyase: The Unique Reaction Mechanism, Physiological Roles, and Therapeutic Applications Against Infectious Diseases and Cancers, Life, 61(11): 1019-1028.*
Hanniffy et al., 2009, Heterologous Production of Methionine—Lyase from *Brevibacterium linens* in *Lactococcus lactis* and Formation of Volatile Sulfur Compounds, Applied and Environmental Microbiology, 75(8): 2326-2332.*
Van Rite et al., 2011, Enzyme prodrug therapy designed to target L-methioninase to the tumor vasculature, Cancer Letters, 301: 177-184.*
Amarita et al., 2004, Identification and Functional Analysis of the Gene Encoding Methionine-_-Lyase in *Brevibacterium linens*, Applied and Environmental Microbiology, 70(12): 7348-7354.*
Dias et al., 1998, Purification and Characterization of L-Methionine _-Lyase from *Brevibacterium linens* BL2, Applied and Environmental Microbiology, 64(9): 3327-3331.*
Cholet et al., 2007, Transcriptional analysis of L-methionine catabolism in *Brevibacterium linens* ATCC9175, Appl. Microbiol. Biotechnol., 74: 1320-1332.*
Database Embl, "Brevibacterium linens L-mehionine-gamma-lyase (mgl) gene, complete cds.", XP002664727, Dec. 10, 2004, retrieved from EBI accession no. EMBL:AY622198, 1 page.
Tan Y, et al., "Polyethylene Glycol Conjugation of Recombinant Methioninase for Cancer Therapy", Protein Expression and Purification, Feb. 1, 1998, pp. 45-52, vol. 12, No. 1, Academic Press, San Diego, CA.
Machover David, et al., "Cytotoxic synergism of methioninase in combination with 5-fluorouracil and folinic acid", Biochemical Pharmacology, Apr. 1, 2001, pp. 867-876, vol. 61, No. 7.
Ashraf S El-Sayed, "Microbial I-methioninase: production, molecular characterization, and therapeutic applications", Applied Microbiology and Biotechnology, Feb. 10, 2010, pp. 445-467, vol. 86, No. 2, Springer, Berlin, DE.
Tan Y, et al., "Serum Methionine depletion without side effects by methioninase in metastatic breast cancer patients", Anticancer Research, Nov. 1, 1996, pp. 3937-3942, vol. 16, No. 6C, International Institute of Anticancer Research, GR.

* cited by examiner

*Primary Examiner* — Amber D Steele
(74) *Attorney, Agent, or Firm* — Whitham Curtis Christofferson & Cook, PC

(57) ABSTRACT

The present invention relates to methods and pharmaceutical compositions for treating cancer. More specifically, the invention relates to a polypeptide isolated from *Brevibacterium aurantiacum* that shows methionine gamma-lyase and homocysteinase activities. The present invention also relates to the use of such a polypeptide for the treatment of cancer.

16 Claims, 6 Drawing Sheets

Figure 1:
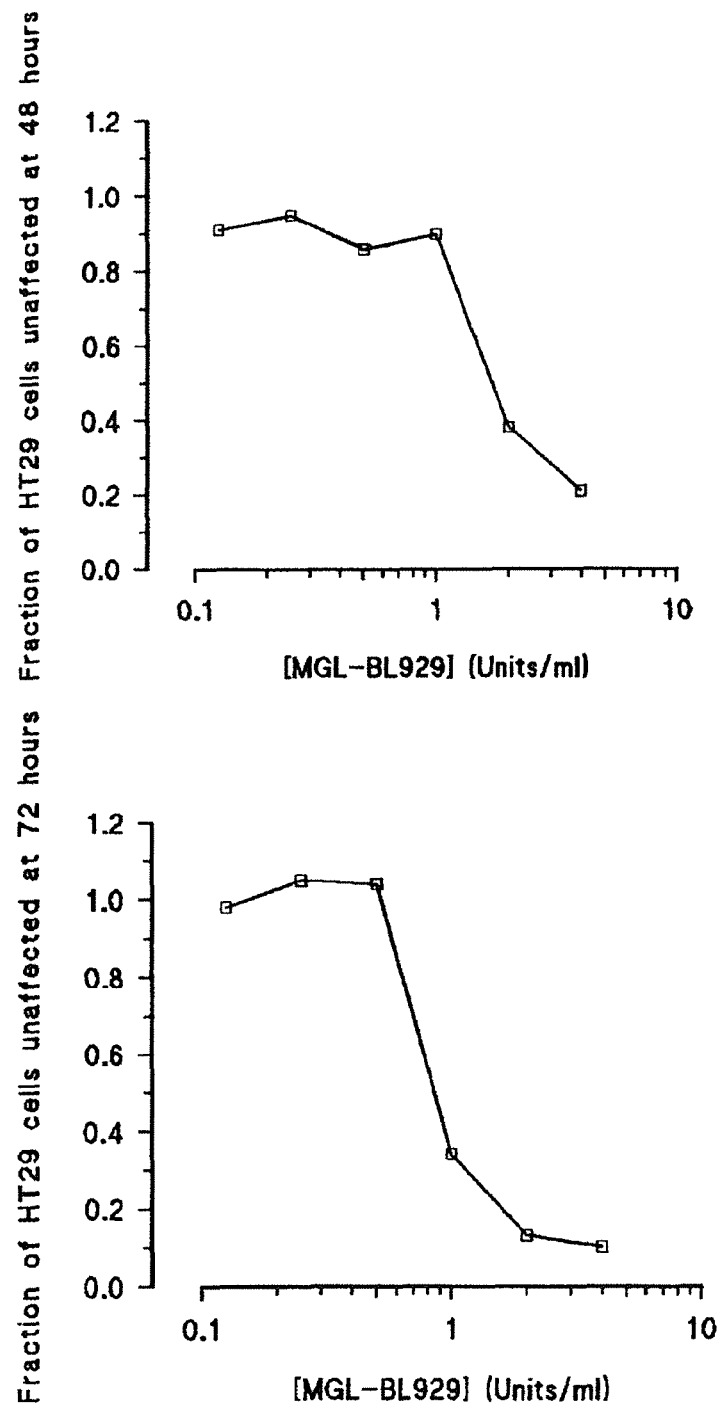

POLYPEPTIDES ISOLATED FROM *BREVIBACTERIUM AURANTIACUM* AND THEIR USE FOR THE TREATMENT OF CANCER

CROSS-REFERENCE TO RELATED APPLICATIONS

This application claims priority to International Application No. PCT/EP2012/061497, filed Jun. 15, 2012, which claims priority to European Application No. 11305748.3, filed Jun. 15, 2011 and U.S. Application No. 61/504,363, filed Jul. 5, 2011, the complete contents of which are herein incorporated by reference.

FIELD OF THE INVENTION

The invention relates to polypdetides isolated from *Brevibacterium aurantiacum* that shows methionine gamma-lyase and homocysteinase activities and their use for the treatment of cancer.

BACKGROUND OF THE INVENTION

Cytotoxicity of cancer cells grown under methionine deprivation has been well established. Depletion of methionine induces death of cancer cells, whereas normal cells are much more resistant. The reasons for this relative selectivity are unknown. Normal and tumor cells can synthesize methionine provided sufficient folate, cobalamin, and homocysteine are supplied. However, most tumor cells require larger amounts of methionine than what they can synthesize, and, in the absence of an exogenous supply, they experience growth inhibition or die.

Depletion of methionine in vitro and in vivo can be achieved through the action of methionine gamma-lyase (L-methionine-α-deamino-γ-mercaptoethane lyase; MGL) that catalyses irreversibly the α,γ-elimination of L-methionine resulting in production of methanethiol, α-ketobutyrate, and ammonia. Various MGLs have been produced by purification from several microorganisms or by recombination of genes encoding for the enzyme originating from various bacterial species and protozoa. Most studies on the antitumor action of methionine depletion have used the MGL from the potentially pathogen pseudomonade, *Pseudomonas putida* (Pp-MGL).

Methionine depletion obtained with Pp-MGL enhances the cytotoxic action of the fluoropyrimidine 5-fluorouracil (FUra), an agent currently used for the treatment of various types of human cancer (Machover et al., 2001; Machover et al., 2002). Potentiation is due to modifications of the intracellular pools of reduced folates induced by methionine depletion and, possibly, through changes in the expression of cellular mechanisms favouring cell death, which may be related to DNA demethylation (Machover et al., 2001; Machover et al., 2002). Other investigators have demonstrated potentiation of FUra and cisplatin in tumor-bearing mice by simultaneous administration of Pp-MGL.

Animal experiments have been performed with the aim to introduce recombinant Pp-MGL in the clinics. However, lethal anaphylactic shock syndromes have been observed when monkeys were re challenged with the protein, which has prevented further development of the native recombinant Pp-MGL. Attempts at reduction of the immunogenicity of the protein through pegylation have not succeeded at the present time.

This pre clinical data believed that the prohibitive immunogenicity of the P.p.MGL, and possibly that of other putative and well characterized MGLs described thus far, which derive all from various micro organisms that are potential pathogens for humans (i.e., originating from the bacteria *Aeromonas* sp., *Citrobacter freundii*, *Porphyromonas gingivalis*, and *Treponema denticola*, and the protozoa *Trichomonas vaginalis*, and *Entamoeba histolytica*), could not allow intra venous administration of the enzyme required for sustained methionine depletion in plasma under safe conditions.

However, there is a need to develop new drugs against cancer. In this way, it has been suggested that characterisation of new therapeutic targets inhibiting tumor cell growth may be highly desirable. There is thus a need in the art for methionine gamma-lyase derived from a non pathogenic micro organism abundantly present in food, this MGL may benefit from oral immune tolerance allowing its administration into the blood stream in a subject in need thereof for treatment of cancer.

SUMMARY OF THE INVENTION

The present invention relates to methods and pharmaceutical compositions for treating cancer. More specifically, the invention relates to *Brevibacterium aurantiacum* methionine gamma-lyase and their use for the treatment of cancer.

DETAILED DESCRIPTION OF THE INVENTION

The present invention relates to the development of methionine gamma-lyase from *Brevibacterium aurantiacum* (ATCC 9175; formerly *Brevibacterium linens*).

The inventors have studied gene expression by transcriptome analysis in the presence of various sulfur-containing amino acids in *B. aurantiacum* (ATCC 9175 a cheese ripening micro organism characterized by aroma and pigment production, and by its property of inhibiting the growth of food pathogens. Surprisingly, these studies led to the identification of the sequence of a new putative methionine gamma-lyase (MGL), greatly different from that previously described in the same micro organism (Amarita et al., 2004).

The inventors have transformed an *E. coli* production strain with an expression plasmid containing the optimized gene of the putative MGL from *B. aurantiacum*. The recombinant enzyme MGL-BL929 produced has shown specific activity for methionine between 4.33 U/mg and 7.21 U/mg, i.e., values near those found for the enzyme derived from *P. putida*. The inventors have demonstrated that MGL-BL929 produced possesses in addition of methionine gamma-lyase activity, homocysteinase activity. The inventors have also demonstrated that MGL-BL929

- depletes methionine and homocysteine from tumor-cell culture media for long periods,
- is stable under tumor cell culture conditions as well as in human serum in vitro,
- possesses high cytotoxic activity against various human tumor cells growing in culture,
- does not affect growth of normal cells at concentrations that are highly cytotoxic for cancer cells,
- potentiates (modulates) the cytotoxic activity of cytostatic agents, and
- circumvents prior cell resistance to cytostatics

DEFINITIONS

The term "methionine gamma-lyase" or "MGL" has its general meaning in the art and refers to L-methionine-α- deamino-γ-mercaptoethane lyase, the enzyme that catalyses irreversibly the α,γ-elimination of L-methionine resulting in production of methanethiol, α-ketobutyrate, and ammonia.

The term "homocysteinase activity" has its general meaning in the art and refers to L-homocysteine lyase activity.

The term "*Brevibacterium linens*" also encompasses three other species, namely *Brevibacterium aurantiacum, Brevibacterium antiquum* and *Brevibacterium permense* as described by Gavrish et al. 2004. Strain ATCC 9175 was deposited as *B. linens* ATCC9175 at the American Type Culture Collection and recently renamed as *B. aurantiacum* ATCC9175 as proposed by Gavrish et al. (2004).

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

By "purified" and "isolated" it is meant, when referring to a polypeptide (i.e. the methionine gamma-lyase of the invention) or a nucleotide sequence, that the indicated molecule is present in the substantial absence of other biological macromolecules of the same type. The term "purified" as used herein preferably means at least 75% by weight, more preferably at least 85% by weight, still preferably at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

The term "PEG" encompasses any polyethylene glycol molecule, without regard to size or to modification at an end of the PEG, and can be represented by the formula X—O(CH$_2$CH$_2$O)n-OH, where n is an integer between 20 and 2300, and X is H or a terminal modification, e.g., alkyl.

By "pegylation" is meant the process by which polyethylene glycol (PEG) chains are attached to polypeptides. The term "pegylated polypeptide" denotes a polypeptide that comprises at least one PEG group covalently conjugated to said polypeptide.

As used herein, the term "subject" denotes a mammal, such as a rodent, a feline, a canine, and a primate. Preferably a subject according to the invention is a human.

Methionine Gamma-Lyase Polypeptides

The invention thus provides an isolated, synthetic or recombinant methionine gamma-lyase polypeptide comprising an amino acid sequence as set forth by SEQ ID NO: 1 or a function-conservative variant thereof.

The present invention thus encompasses function-conservative variants of the methionine gamma-lyase polypeptides as set forth by SEQ ID NO:1. The function-conservative variants may result from modifications and changes that may be made in the structure of the polypeptides of SEQ ID NO:1 (and in the DNA sequences encoding it), and still obtain a functional molecule with desirable characteristics (MGL and homocysteinase).

Accordingly, "function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The amino acid changes may be achieved by changing codons in the DNA sequence, according to Table 1.

TABLE 1

| Amino acids | | | Codons |
|---|---|---|---|
| Alanine | Ala | A | GCA, GCC, GCG, GCU |
| Cysteine | Cys | C | UGC, UGU |
| Aspartic Acid | Asp | D | GAC, GAU |
| Glutamic acid | Glu | E | GAA, GAG |
| Phenylalanine | Phe | F | UUC, UUU |
| Glycine | Gly | G | GGA, GGC, GGG, GGU |
| Histidine | His | H | CAC, CAU |
| Isoleucine | Ile | I | AUA, AUC, AUU |
| Lysine | Lys | K | AAA, AAG |
| Leucine | Leu | L | UUA, UUG, CUA, CUC, CUG, CUU |
| Methionine | Met | M | AUG |
| Asparagine | Asn | N | AAC, AAU |
| Proline | Pro | P | CCA, CCC, CCG, CCU |
| Glutamine | Gln | Q | CAA, CAG |
| Arginine | Arg | R | AGA, AGG, CGA, CGC, CGG, CGU |
| Serine | Ser | S | AGC, AGU, UCA, UCC, UCG, UCU |
| Threonine | Thr | T | ACA, ACC, ACG, ACU |
| Valine | Val | V | GUA, GUC, GUG, GUU |
| Tryptophan | Trp | W | UGG |
| Tyrosine | Tyr | Y | UAU |

For example, certain amino acids may be substituted for other amino acids in a protein structure without appreciable loss of methionine gamma-lyase capability or homocysteinase capability. Since it is the interactive capacity and nature of a protein that defines that protein's biological functional activity, certain amino acid substitutions can be made in a protein sequence, and, of course, in its DNA encoding sequence, and nevertheless obtain a protein with like properties. It is thus contemplated that various changes may be made in the polypeptide sequences of the invention, or corresponding DNA sequences which encode said polypeptides, without appreciable loss of their biological activity.

Said methionine gamma-lyase activity and homocysteinase activity can be assessed by different techniques well-known in the art as described hereinafter.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The methionine gamma-lyase activity and homocysteinase activity of the function-conservative variants may be assessed according any method of assaying methionine gamma-lyase activity and homocysteinase activity known in the art, such as for instance the assays referred in the instant application.

The polypeptides of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Polypeptides of the invention can be use in an isolated (e.g., purified) form or contained in a vector, such as a membrane or lipid vesicle (e.g. a liposome).

In specific embodiments, it is contemplated that polypeptides according to the invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

For example, Pegylation is a well established and validated approach for the modification of a range of polypeptides (Chapman, 2002). The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein (Cunningham-Rundles et. al., 1992); and (e) improved thermal and mechanical stability of the PEGylated polypeptide.

Therefore, advantageously, the polypeptides of the invention may be covalently linked with one or more polyethylene glycol (PEG) group(s).

Accordingly, one aspect of the invention provides modified polypeptides, wherein the modification comprises a single polyethylene glycol group covalently conjugated to the polypeptide. Other aspects provide modified polypeptides covalently conjugated to one, two, three, or more polyethylene glycol groups. The one or more PEG may have a molecular weight ranging from about 1 kDa to about 100 kDa, and will preferably have a molecular weight ranging from about 10 to about 60 kDa or about 10 to about 40 kDa. One skilled in the art can select a suitable molecular mass for PEG, based on how the pegylated polypeptide will be used therapeutically by considering different factors including desired dosage, circulation time, resistance to proteolysis, immunogenicity, etc.

In one embodiment, the PEG of the invention terminates on one end with hydroxy or methoxy, i.e., X is H or $CH_3$ ("methoxy PEG"). In addition, such a PEG can consist of one or more PEG side-chains which are linked together. PEGs with more than one PEG chain are called branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. One form of PEGs includes two PEG side-chains (PEG2) linked via the primary amino groups of a lysine (Monfardini, et al., 1995).

To effect covalent attachment of PEG groups to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidyl carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g. from Shearwater Polymers, Inc., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPDX-PEG, NCO-PEG, NPC-PEG, CDI-PEG, ALD-PEG, TRES-PEG, VS-PEG, IODO-PEG, and MAL-PEG, and branched PEGs such as PEG2-NHS.

The conjugation of the polypeptide and the activated polymer molecules is conducted by use of any conventional method. Conventional methods are known to the skilled artisan. The skilled person will be aware that the activation method and/or conjugation chemistry to be used depends on the attachment group(s) of the polypeptides as well as the functional groups of the PEG molecule (e.g., being amine, hydroxyl, carboxyl, aldehyde, ketone, sulfhydryl, succinimidyl, maleimide, vinylsulfone or haloacetate).

In one embodiment, polypeptides are conjugated with PEGs at amino acid D and E (for COOH), T, Y and S (for OH), K (for $NH_2$), C (for SH if at least one cysteine is conserved) or/and Q and N (for the amide function).

In one embodiment, additional sites for PEGylation can be introduced by site-directed mutagenesis by introducing one or more lysine residues. For instance, one or more arginine residues may be mutated to a lysine residue. In another embodiment, additional PEGylation sites are chemically introduced by modifying amino acids on polypeptides of the invention.

In one embodiment, PEGs are conjugated to the polypeptide through a linker. Suitable linkers are well known to the skilled person. A preferred example is cyanuric chloride (Abuchowski et al., 1977; U.S. Pat. No. 4,179,337).

Conventional separation and purification techniques known in the art can be used to purify pegylated polypeptides of the invention, such as size exclusion (e.g. gel filtration) and ion exchange chromatography. Products may also be separated using SDS-PAGE.

In one embodiment, the pegylated polypeptides provided by the invention have a serum half-life in vivo at least 50%, 75%, 100%, 150% or 200% greater than that of an unmodified polypeptide.

In another embodiment the polypeptides of the invention are covalently coupled to a tumor targeting agent as well known in the art.

Non limiting examples include but are not limited to antibodies directed against the EDB domain of fibronectin, antibodies or agents binding Vascular endothelial growth factor receptor 2, antibodies or molecules binding fibroblast growth factor receptor-1, antibodies or agents that interact with CD31, antibodies or agents interacting with tumor lymphatic endothelium (Podoplanin, Lyve-1), or antibodies or agents binding to αVβ3 integrin such as RGD peptides, or antibodies or agents interacting with tumor membrane-bound and intracellular targets.

Nucleic Acids, Vectors and Recombinant Host Cells

Another object of the invention relates to an isolated, synthetic or recombinant nucleic acid encoding for a methionine gamma-lyase polypeptide according to the invention. In a particular embodiment, said nucleic acid comprises a sequence as set forth by SEQ ID NO: 2. In another particular embodiment, said nucleic acid comprises a sequence as set forth by SEQ ID NO: 3.

Typically, said nucleic acid is a DNA or RNA molecule, which may be included in any suitable vector, such as a plasmid, cosmid, episome, artificial chromosome, phage or a viral vector. The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, another object of the invention relates to a vector comprising a nucleic acid of the invention.

Such vectors may comprise regulatory elements, such as a promoter, enhancer, terminator and the like, to cause or direct expression of said polypeptide upon administration to a subject. The vectors may further comprise one or several origins of replication and/or selectable markers. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like.

Examples of plasmids include replicating plasmids comprising an origin of replication, or integrative plasmids, such as for instance pUC, pcDNA, pBR, and the like. Examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCR1P cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

Another object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). More particularly, the invention contemplates vascular or endothelial cells thereof or derived thereof, such as human umbilical vein endothelial (HUVEC) or progenitor endothelial cells (PEC).

The present invention also relates to a method for producing a recombinant host cell expressing a methionine gamma-lyase polypeptide according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said methionine gamma-lyase polypeptide. Such recombinant host cells can be used for the production of methionine gamma-lyase polypeptides according to the present invention, as previously described.

The invention further relates to a method of producing a methionine gamma-lyase polypeptide according to the invention, which method comprises the steps consisting of: (i) culturing a transformed host cell according to the invention under conditions suitable to allow expression of said methionine gamma-lyase polypeptide; and (ii) recovering the expressed polypeptide.

Therapeutic Methods and Uses

In one embodiment, the invention provides a method for treating cancer comprising administering a subject in need thereof with a therapeutically effective amount of a polypeptide or nucleic acid of the invention.

In the context of the invention, the term "treating" or "treatment", as used herein, means reversing, alleviating, inhibiting the progress of, or preventing the disorder or condition to which such term applies, or one or more symptoms of such disorder or condition.

According to the invention, the term "subject" or "subject in need thereof", is intended for a human or non-human mammal affected or likely to be affected with a cancer.

By a "therapeutically effective amount" of the polypeptide of the invention is meant a sufficient amount of the polypeptide to treat a cancer, (for example, to limit tumor growth or to slow or block tumor metastasis) at a reasonable benefit/risk ratio applicable to any medical treatment. It will be understood, however, that the total daily usage of the polypeptides and compositions of the present invention will be decided by the attending physician within the scope of sound medical judgment. The specific therapeutically effective dose level for any particular subject will depend upon a variety of factors including the disorder being treated and the severity of the disorder; activity of the specific polypeptide employed; the specific composition employed, the age, body weight, general health, sex and diet of the subject; the time of administration, route of administration, and rate of excretion of the specific polypeptide employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

In a particular embodiment the polypeptide or nucleic acid of the invention may be administered concomitantly with one or more agents required for function of the polypeptide, such as enzyme cofactors. For example, said enzyme cofactor is a pyridoxal phosphate.

In a particular embodiment the polypeptide or nucleic acid of the invention may be administered sequentially or concomitantly with one or more chemotherapeutic or radiotherapeutic agents.

In one embodiment said chemotherapeutic or radiotherapeutic agents are a therapeutic active agent used as anticancer agent. For example, said anticancer agents include but are not limited to fludarabine, gemcitabine, capecitabine, methotrexate, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbazine, epipodophyllotoxins such as etoposide and teniposide, camptothecins such as irinotecan and topotecan, bleomycin, doxorubicin, idarubicin, daunorubicin, dactinomycin, plicamycin, mitoxantrone, L-asparaginase, doxorubicin, epirubicin, 5-fluorouracil and 5-fluorouracil combined with leucovorin, taxanes such as docetaxel and paclitaxel, levamisole, estramustine, nitrogen mustards, nitrosoureas such as carmustine and lomustine, vinca alkaloids such as vinblastine, vincristine, vindesine and vinorelbine, imatinib mesylate, hexamethylmelamine, kinase inhibitors, phosphatase inhibitors, ATPase inhibitors, tyrphostins, protease inhibitors, inhibitors herbimycin A, genistein, erbstatin, and lavendustin A. In one embodiment, additional anticancer agents may be selected from but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxins, hormonal therapies, retinoids, photosensitizers or photodynamic therapies, angiogenesis inhibitors, antimitotic agents, isoprenylation inhibitors, cell cycle inhibitors, actinomycin, bleomycin, anthracyclines, MDR inhibitors and $Ca^{2+}$ ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Further therapeutic active agent can be an antiemetic agent. Suitable antiemetic agents include, but are not limited to, metoclopramide, domperidone, prochlorperazine, promethazine, chlorpromazine, trimethobenzamide, ondansetron, granisetron, hydroxyzine, acetylleucine, alizapride, azasetron, benzquinamide, bietanautine, bromopride, buclizine, clebopride, cyclizine, dimenhydrinate, diphenidol, dolasetron, meclizine, methallatal, metopimazine, nabilone, pipamazine, scopolamine, sulpiride, tetrahydrocannabinols, thiethylperazine, thioproperazine and tropisetron. In a preferred embodiment, the antiemetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the other therapeutic active agent can be an opioid or non-opioid analgesic agent. Suitable opioid analgesic agents include, but are not limited to, morphine, heroin, hydromorphone, hydrocodone, oxymorphone, oxycodone, metopon, apomorphine, buprenorphine, meperidine, loperamide, ethoheptazine, betaprodine, diphenoxylate, fentanyl, sufentanil, alfentanil, remifentanil, levorphanol, dextromethorphan, phenazone, pemazocine, cyclazocine, methadone, isomethadone and propoxyphene. Suitable non-opioid analgesic agents include, but are not limited to, aspirin, celecoxib, rofecoxib, diclofenac, diflunisal, etodolac, fenoprofen, flurbiprofen, ibuprofen, ketoprofen, indomethacin, ketorolac, meclofenamate, mefenamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, clorazepate, clonazepam, chlordiazepoxide and alprazolam.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

Pharmaceutical Composition

Another object of the invention relates to a pharmaceutical composition comprising a polypeptide or nucleic acid according to the invention and a pharmaceutically acceptable carrier.

Typically, polypeptide or nucleic acid according to the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The methionine gamma-lyase can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The methionine gamma-lyase may be formulated within a therapeutic mixture to comprise about 0.0001 to 1.0 milligrams, or about 0.001 to 0.1 milligrams, or about 0.1 to 1.0 milligrams, or about 1 to 10 milligrams or even about 10 to 100 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Another object of the invention relates to a pharmaceutical composition according to the invention comprising one or more enzyme cofactors. For example, said enzyme cofactor is a pyridoxal phosphate.

Another object of the invention relates to a pharmaceutical composition according to the invention comprising one or more chemotherapeutic or radiotherapeutic agents.

The invention will be further illustrated by the following examples and figures. However, these examples and figures should not be interpreted in any way as limiting the scope of the present invention.

FIGURES

FIG. 1: Dose-effect cytotoxicity curve of the recombinant MGL-BL929 in HT29 human colon carcinoma cell line exposed to the enzyme for 48 hr. and 72 hr.

Figure 2:
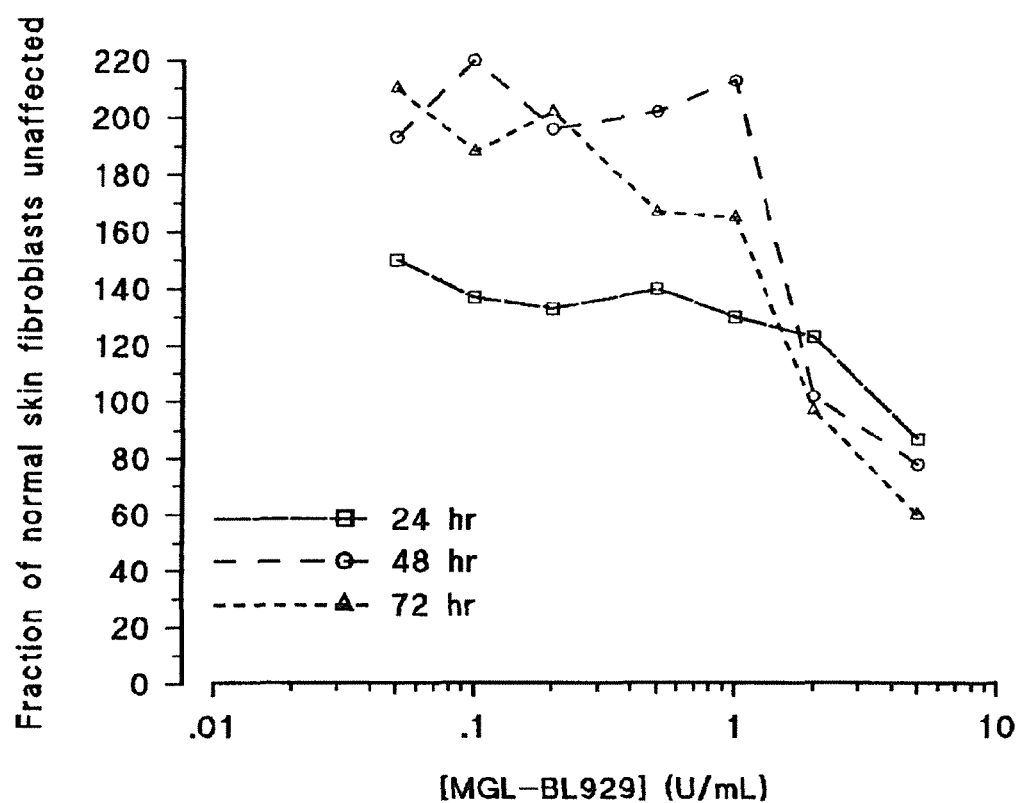

FIG. 2: Dose-effect cytotoxicity curve of the recombinant MGL-BL929 in normal skin fibroblasts exposed 48 hr. and 72 hr. to the enzyme.

Figure 3A:
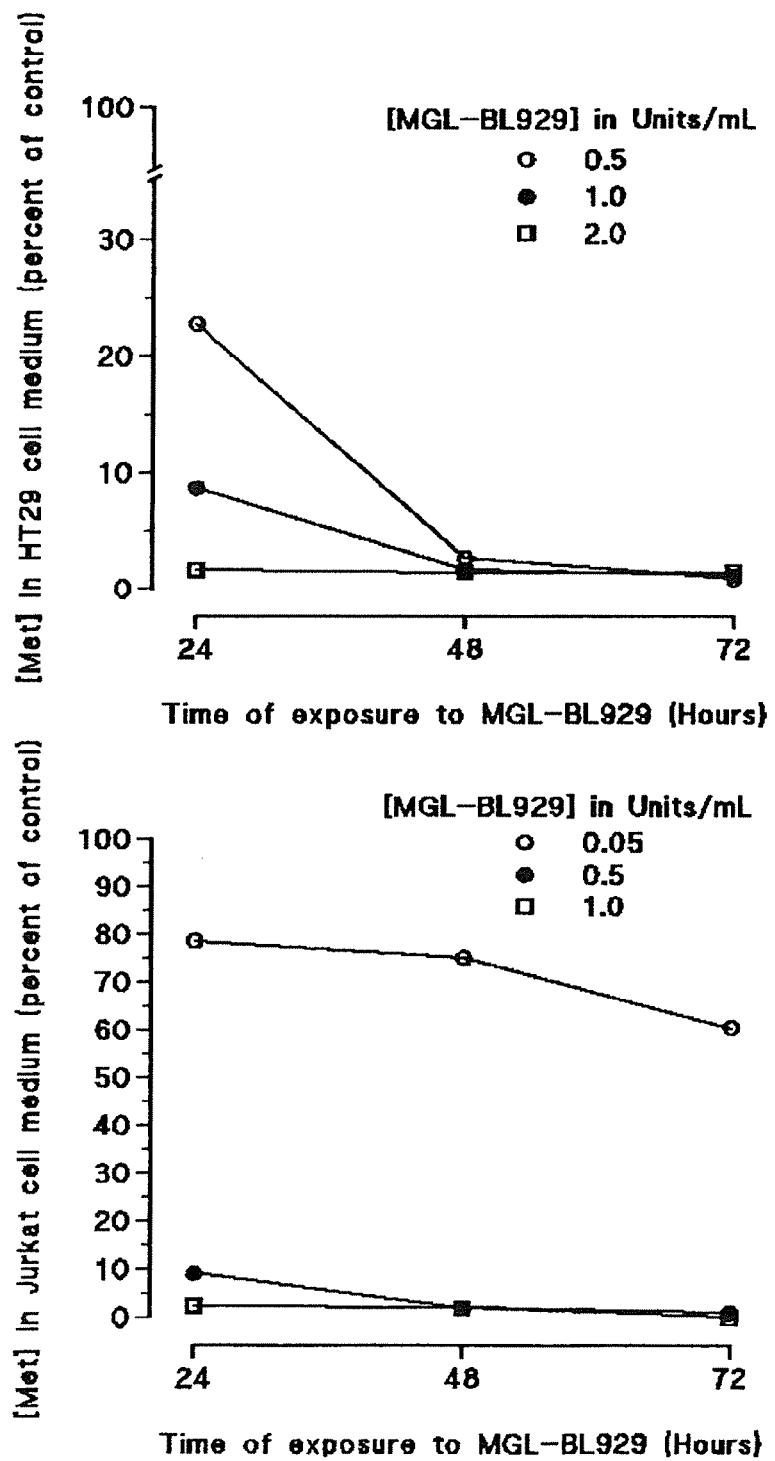
Figure 3B:
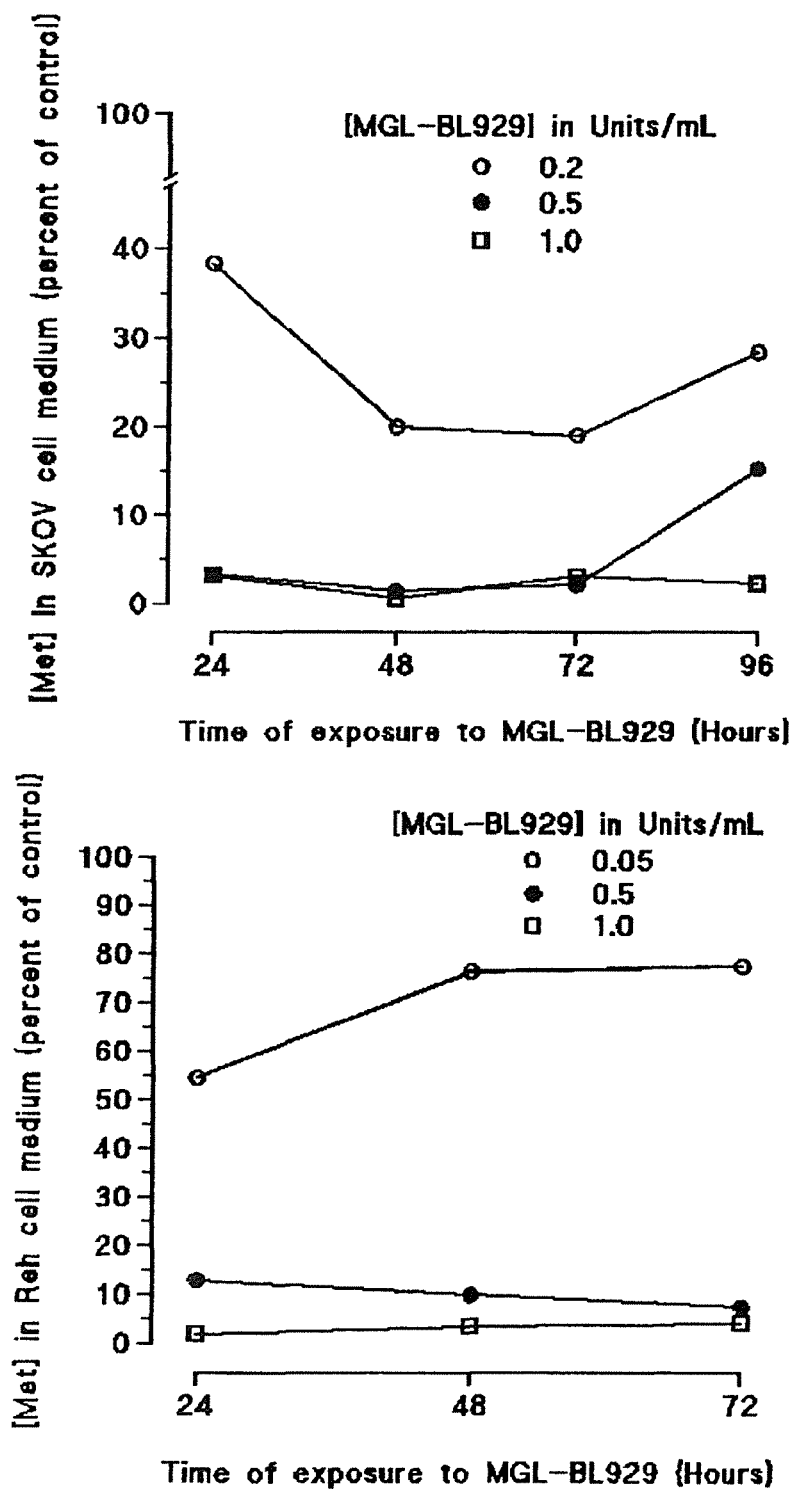

FIG. 3A-B: Concentration (expressed in percent of control) of L-methionine in the supernatant of HT29, SKOV3, Jurkat, and Reh human tumor cell cultures exposed to various concentrations of MGL-BL929.

Figure 4A:
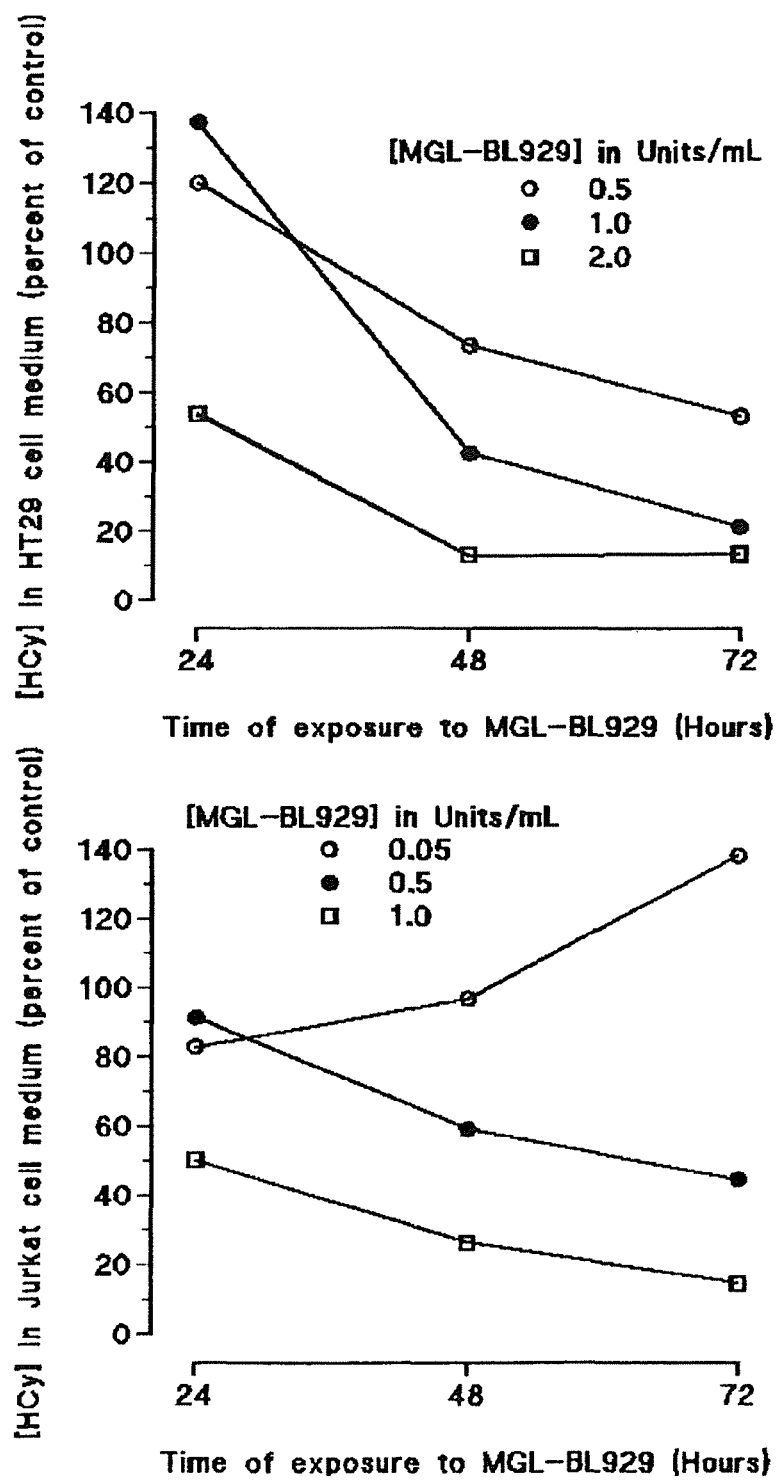
Figure 4B:
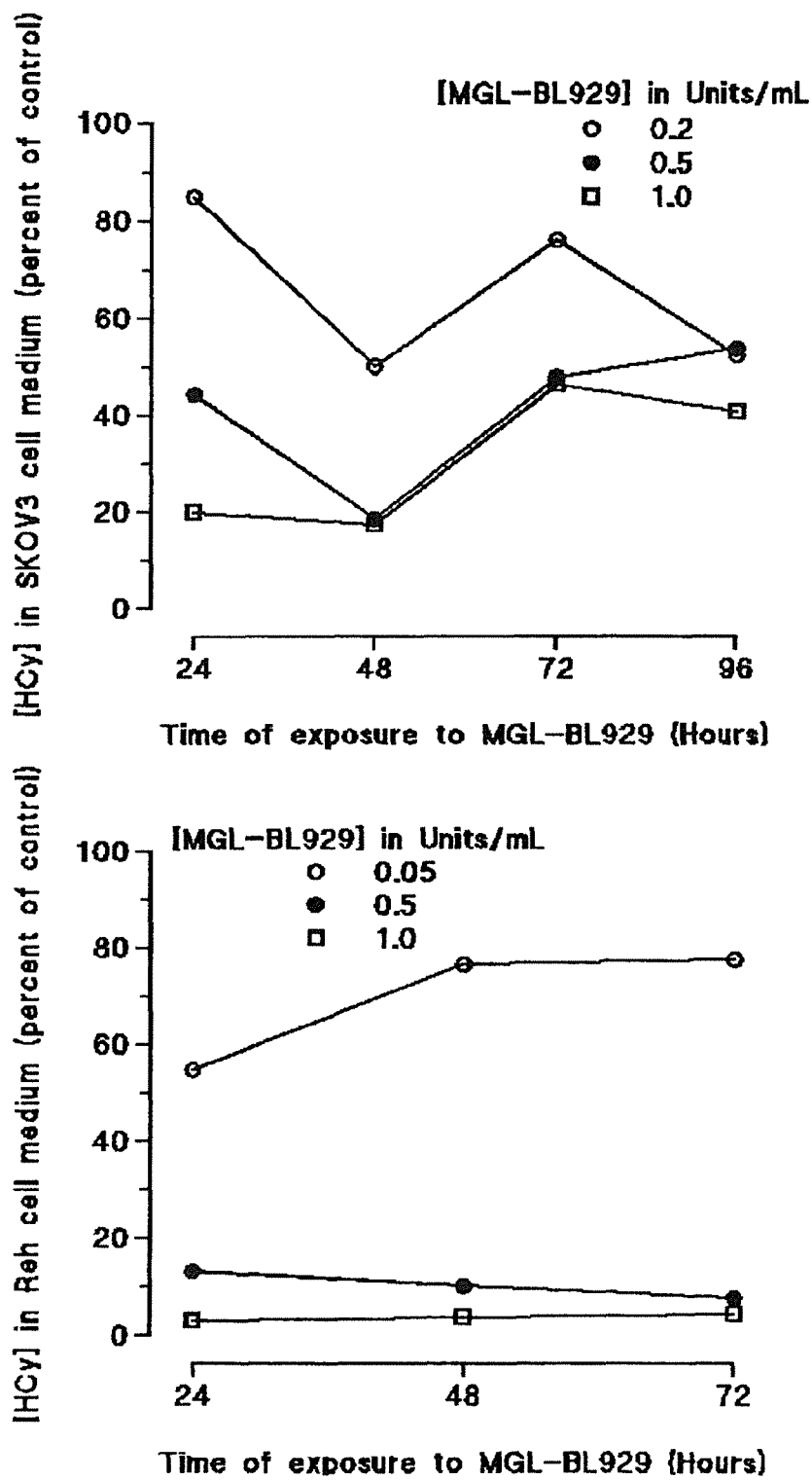

FIG. 4A-B: Concentration (expressed in percent of control) of L-homocysteine in the supernatant of HT29, SKOV3, Jurkat, and Reh human tumor cell cultures exposed to various concentrations of MGL-BL929.

EXAMPLES

Materials and Methods

Methods:

Characterization of the Methionine Gamma-Lyase (MGL-BL929) from *Brevibacterium aurantiacum* (*B. aurantiacum*; ATCC 9175; Formerly *B. linens*)

Various aspects of metabolism and gene expression were studied by transcriptome analysis of *Brevibacterium aurantiacum* (ATCC 9175) cultured in the absence and in the presence of various sulfur-containing amino acids. Studies led to identification within the *B. aurantiacum* genome of a gene (BL929) encoding a putative MGL.

Production of the *Brevibacterium aurantiacum* Methionine Gamma-Lyase (MGL-BL929)

Bacterial Strain and Growth Production

The *Escherichia coli* BL21 (DE3) production strain (Agilent technologies, Santa Clara, Calif.) was grown in Erlenmeyer at 30° C. with 200-250 rpm shaking in reconstituted Luria Bertani (LB) broth: 1% tryptone, 5% yeast extract (Fluka, St Louis Mo.), 1% NaCl resuspended in pure water, supplemented with 50 µg/mL kanamycin when necessary. Solid media were prepared by adding technical agar (Invitrogen, Paisley, UK) at a final concentration of 1.5% w/v.

Production and Purification of the *Brevibacterium aurantiacum* Methionine Gamma-Lyase MGL-BL929

The open reading frame (ORF) encoding MGL-BL929 from *B. aurantiacum* was optimized in order to adapt *B. aurantiacum* codon usage to *E. coli* expression system (SEQ ID NO: 3). The optimized gene was synthesized and sub cloned into an *E. coli* subcloning vector given pMA-BL929, according to GeneART standard procedures. The BL929 ORF was digested by restriction enzymes NdeI and XbaI from pMA-BL929 and ligated into *E. coli* pGTPc608a expression vectors (pET9d derivative carrying PTac promoter, Lac operator, a multiple cloning site, LacIq and T1T2 terminator) previously digested by the same enzymes. Ligation mixture was transformed into electro-competent cells of *E. coli* DH5α strains. The resulting plasmids pGTPc608-BL929 were verified by digestion and sequencing. Restriction enzymes, T4 DNA ligase and Antartic phosphatase (New England Biolabs, Ipswich, Mass.), high fidelity Phusion™ DNA polymerase (Finnzymes, Espoo, Finland) were used according to recommendations of the manufacturers. DNA purification kits were purchased from Macherey-Nagel (Düren, Germany). Sequencing was performed by Genome Express (Meylan, France).

The *E. coli* production strain BL21 (DE3) was transformed with the expression plasmid pGTPc608-BL929. A single colony carrying pGTPc608-BL929 was grown at 37° C. in a 70 L Applikon bioreactor containing 35 L of GYP medium (yeast extract 24 g/L, soy peptone 12 g/L, $KH_2PO_4$ 4.8 g/L, $K_2HPO_4$ 2.2 g/L and glycerol 5 g/L) supplemented with 0.02% pyridoxal 5'-phosphate. Expression was induced by 0.1 mM IPTG when the culture reached an $OD_{600nm}$ of 2. When initial glycerol was totally depleted, concentrated feeding-solution (30% w/v glycerol and 30% w/v yeast extract) was added by a remote controlled pump. The pump flow rate was regulated based on pH set point. Cells were harvested when the culture $OD_{600nm}$ reached 40-50.

Cells were suspended in lysis buffer (20 mM Tris, 1 mM PMSF, 1 mM EDTA, 1 mM DTT, 0.1 mM pyridoxal 5'-phosphate, pH 7.5) and lysed by high pressure homogenization. The cell extract was clarified by centrifugation for 30 min at 15,900 g at 4° C. then filtered through a 0.45 µm low level protein binding disposable filter (Sartorius, Gottingen, Germany). Solid ammonium sulphate (AS) was added to the cell extract to reach a final concentration of 0.75 M and stirred at 4° C. for 16 hours. The sample was centrifuged at 15,900 g for 30 min at 4° C., then filtered with a 0.45 µm low level protein binding disposable filter to remove all precipitated proteins before being injected in a column of Phenyl Sepharose (High Sub) 6 Fast Flow resin (GE Healthcare). The column was equilibrated with 20 mM Tris, 0.75 M AS, 0.1 mM PLP, pH 7.5. Proteins were eluted by decreasing the AS concentration in several steps from 100% to 0%. The elution fractions containing MGL-BL929 were pooled, concentrated 5-fold using an ultrafiltration cassette with a cut-off of 10 kDa, then diafiltered versus 7 volumes of 20 mM Bis Tris, 0.1 mM PLP, pH 6.0 (Pall, Port Washington, N.Y.).

The Hydrophobic Interaction Chromatography (HIC) elution was passed through a column packed with DEAF Sepharose Fast Flow resin (GE Healthcare) pre equilibrated in 20 mM Bis Tris, 0.1 mM PLP, pH 6.0. Proteins were eluted by increasing NaCl concentration in several steps from 0 to 1

M. The elution fractions containing MGL-BL929 were collected, concentrated 3 fold using an ultra-filtration cassette (Pall, Port Washington, N.Y.) then diafiltered versus 7 volumes of 40 mM Na*PO4, 20 µM PLP, pH 7.5.

The DEAF elution was clarified by filtration through a 0.2 µm low level protein binding disposable filter (Corning, Union City, Calif.). Endotoxins were removed by filtration through a Mustang E capsule (Pall, Port Washington, N.Y.). The concentration of MGL-BL929 was achieved using a stirred cell containing a membrane with a cut-off of 10 kDa in order to reach a final concentration range between 20 and 30 mg/mL (Millipore, Billerica, Mass.). The purified protein was stored at −80° C. Enzyme concentration and purity were determined by capillary electrophoresis, SDS PAGE and Bradford assay. The oligomerization state of the purified enzyme was investigated by Size Exclusion Chromatography (SEC) using a Superdex 200 5/150 GL column (GE Healthcare). Endotoxin concentration of the final product was assayed by Lonza (Testing services).

Enzyme Assays

The ability of the purified enzyme to catalyze $\alpha,\gamma$ elimination reactions against amino acids and substituted amino acids was tested separately with L-methionine, L-homocysteine, L-cysteine, L-cystathionine, S-adenosyl L-methionine, S-adenosyl L-homocysteine, and D-methionine. Activity was measured by incubating the enzyme in 100 mM K*PO$_4$, 0.01 mM PLP, pH 7.5 with 25 mM of substrate in a final volume of 1 mL. The mixture was incubated at 25° C. for 10 min, and the reaction was stopped by addition of trichloroacetic acid to a final concentration of 5%. The $\alpha$-ketobutyrate formed in the supernatant solution was measured with 3-methyl-2-benzothiazolone hydrazone using spectrophotometry at 320 nm (Soda et al., 1967).

Cytotoxicity Studies and Cell Lines

Seven human tumor cell lines were used to determine the cellular effects of MGL-BL929. These comprise five adherent solid tumor-derived cell lines (including the colorectal carcinoma cell line HT29, two stable variants of HT29 selected for their high levels of resistance to methotrexate (HT29$_{MTX}$), and to fluorouracil (HT29$_{FUra}$), the ovarian carcinoma cell line SKOV3, and the hepatoblastoma-derived cell line (HepG2), and 2 non-adherent tumor cell lines (including the T-cell lymphoma cell line Jurkat, and the acute lymphocytic leukemia cell line Reh). Similarly, human non-tumor skin fibroblasts (CDGII) were exposed to MGL-BL929 at various concentrations in order to explore selectivity of MGL-BL929 towards cancer cells.

The cells lines were thawed from mycoplasma-free frozen stocks and were controlled for contamination. Cells were maintained in cell culture medium (RPMI 1640 or DMEM according to the growth requirements of each cell line), supplemented with 10% FBS and antibiotics (streptomycin, 50 µg/mL, and penicillin, 50 U/mL) at 37° in an atmosphere containing 5% CO$_2$. Cells were exposed in 12 well-cell plates to the purified recombinant MGL-BL929 at a concentration range from 0.05 U/mL to 5 U/mL, and were harvested 24 hr., 48 hr., 72 hr., and 96 hr. from start of the exposure. Cell viability was measured with the Trypan blue dye exclusion test in Malassez chambers.

Measurement of L-Methionine and L-Homocysteine in Cell Culture

The concentrations of L-methionine and L-homocysteine were measured in the supernatant of HT29, SKOV3, Jurkat, and Reh cell cultures growing exponentially in cell culture medium supplemented with 10% FBS, exposed at t0 to various concentrations of MGL-BL929 for 24 hr., 48 hr., 72 hr., and 96 hr. HT29 was grown in DMEM, and the three other cell lines were in RPMI 1640 cell culture medium. Measurements were done by ion-exchange chromatography. (N.B., concentrations of L-homocysteine in RPMI 1640, and in DMEM cell culture media are 101 µmol/L, and 201 µmol/L, respectively).

Studies of Protein Stability by Western Blot

Fractions of the supernatants of HT29 cells in culture exposed to various concentrations of the recombinant MGL-BL929 were subjected to SDS-PAGE under denaturing conditions, and then revealed by Western Blot (WB) with a polyclonal rabbit anti MGL-BL929 serum that was generated against the purified enzyme Western Blot analysis was also performed in human scrum incubated with the purified recombinant MGL-BL929 for 72 hr.

Results:

Characterization of the Methionine Gamma-Lyase (MGL-BL929) from *Brevibacterium aurantiacum* (*B. aurantiacum*; ATCC 9175; Formerly *B. linens*)

Comparisons of *Brevibacterium aurantiacum* (ATCC 9175) gene expression profiles in the presence of L-cystine and L-cystine plus L-methionine showed up-regulation of two adjacent genes in the presence of methionine, including the gene BL929 encoding a putative MGL. Up-regulation of BL929 was accompanied by the production of large amounts of volatile sulfur compounds resulting from degradation of methionine (Forquin et al., 2010).

The sequence of the putative BL929 gene was identified within the genome of *B. linens* (*Brevibacterium linens* BL2 NZ_AAGP01000007, whole genome shotgun sequence). The genome comprises 115535 base pairs (bp). The putative MGL nucleotide sequence BL929 is at position 34415 and is composed of 1182 bp (34415 to 35596) (SEQ ID NO: 2). The reference of the sequence of the translated protein is ZP_05913004.1 (SEQ ID NO: 1).

Purification

Purification of MGL-BL929 was achieved to homogeneity from a 5 L scale cell pellet after four successive chromatography steps (Table 1). The purification schema allowed purifying 1.2 g of MGL-BL929 with a degree of protein purity of 94% containing very low levels of endotoxin, corresponding to a recovery rate of 23%.

TABLE 1

Purification of MGL-BL929 from *Brevibacterium aurantiacum* (ATCC 9175).

| Purification step | Total conc. (mg/mL) | [MGL-BL929] (mg/mL) | MGL-BL929 % purity | Amount (g) | Recovery Process (%) | Recovery Step (%) |
|---|---|---|---|---|---|---|
| Cell extract | 5.7 | 1.4 | 24 | 5.1 | | |
| (NH$_4$)$_2$SO$_4$ Precipitation | 3.4 | 1.1 | 32 | 3.9 | 76 | 76 |
| Phenyl Sepharose HIC | 0.2 | 0.1 | 64 | 2.5 | 49 | 64 |
| Concentration Diafiltration FF | 4.0 | 1.4 | 70 | 2.1 | 41 | 85 |
| DEAE Sepharose AEC | 1.1 | 0.9 | 81 | 1.3 | 25 | 60 |

TABLE 1-continued

Purification of MGL-BL929 from *Brevibacterium aurantiacum* (ATCC 9175).

| Purification step | Total conc. (mg/mL) | [MGL-BL929] (mg/mL) | MGL-BL929 % purity | Amount (g) | Recovery Process (%) | Recovery Step (%) |
|---|---|---|---|---|---|---|
| Concentration Diafiltration UF | 2.2 | 2.2 | 98 | 1.0 | 20 | 80 |
| Mustang E | 1.6 | 1.6 | 100 | 0.9 | 17 | 86 |
| Concentration | 23.7 | 22.3 | 94 | 1.2 | 23 | 100 |

Enzyme Size

The molecular weight of the native enzyme was investigated by size exclusion chromatography (SEC). The hydrodynamic volume of the purified MGL-BL929 corresponds to a 171.5 kDa globular protein. Since the molecular weight of MGL-BL929 determined by capillary electrophoresis under denaturing conditions is 46.5 kDa, the results suggest that MGL-BL929 is a monodisperse homotetrameric species.

Substrate Specificity

Enzymatic activity of the purified MGL-BL929 on various substrates was determined by measurement of α-ketoacids produced (Soda et al., 1967). The purified enzyme catalyzed the α,γ-elimination of L-methionine and L-homocysteine (Table 2). The enzyme had no activity towards L-cysteine, L-cystathionine, S-adenosyl-L-homocysteine and D-methionine. Affinity and specific activity of the purified MGL-BL929 for L-homocysteine were 7.3-fold, and 4.8-fold greater than that measured for L-methionine, respectively.

TABLE 2

Substrate specificity and enzymatic activity of the purified MGL-BL929 from *Brevibacterium aurantiacum*.

| Substrate | Km (mM) | Vmax (μmol · min$^{-1}$ · m$^{-1}$) |
|---|---|---|
| L-Homocysteine | 0.94 ± 0.8 | 27.7 ± 5.7 |
| L-Methionine | 6.83 ± 2.4 | 5.77 ± 1.4 |
| L-Cysteine | 0 | 0 |
| L-Cystathionine | 0 | 0 |
| S-Adenosyl L-homocysteine | 0 | 0 |
| D-methionine | 0 | 0 |

One unit of enzyme is the amount that catalyzes the formation of 1 μmol of α-ketobutyrate per minute The Purified MGL-BL929 Exerts Strong Cytotoxic Activity Against Human Tumor Cell Lines Growing in Culture.

MGL-BL929 Cytotoxicity appeared in most cell lines at levels greater than 0.5 U/mL of MGL-BL929 and was augmented with increasing concentrations of the enzyme. Table 3 summarizes the IC50 for each cell line at 72 hours of exposure, representing the concentration of the recombinant MGL-BL929 (in Units/mL) achieving 50% growth inhibition in tumor and normal cells.

The IC50s differ in the various tumor cell lines; they are lowest in lymphoma- and leukemia-derived cells and the standard colon carcinoma HT29 cells. In the other tumor-derived cells, the IC50s are comprised between 1 and 1.5 U/mL. Interestingly, the IC50 for MGL-BL929 in HT29$_{MTX}$ was low (0.3 U/mL) when cells were simultaneously exposed to the enzyme and to 1 μM methotrexate (MTX) to which they are fully resistant, which suggests that MGL-BL929 may overcome prior resistance to cytostatic agents. Results highly suggesting potentiation of 5-fluorouracil (FUra) by MGL-BL929 have been obtained in the human colon carcinoma cell line HT29. From these results, the inventors conclude that MGL-BL929 is able to potentiate the cytotoxicity of cytostatic agents and can overcome prior resistance to these compounds.

TABLE 3

Growth inhibition in human cell lines in vitro exposed to the recombinant MGL-BL929 from *Brevibacterium aurantiacum* (ATCC 9175).

| Type of Cell | IC50[2] of MGL-BL929 in tumor cell lines and normal fibroblasts exposed for 72 hours to the enzyme (in Units/mL)[1] |
|---|---|
| HT29 | 0.9 |
| HT29$_{MTX}$ | 1.5 (0.3)[3] |
| HT29$_{5-FU}$ | 1.2 |
| SKOV3 | 1 |
| HepG2 | 1.2 |
| Jurkat | 0.6 |
| Reh | 0.9 |
| Normal Skin Fibroblasts | >4 |

[1]One unit of MGL-BL929 is the amount that catalyzes the formation of 1 μmol of α-ketobutyrate per minute
[2]IC50s for each cell type are extrapolated from the concentration-response curve
[3]IC50 of MGL-BL929 in HT29$_{MTX}$ simultaneously exposed to 1 μM methotrexate (MTX) to which cells are fully resistant.

Exposure to MGL-BL929 of human non tumor fibroblasts CDGII affect their growth only at concentration levels greatly higher than that required for cytotoxicity of cancer cells. The inventors did not observe any measurable decrease in number of cells exposed to MGL-BL929 at concentrations up to 4 U/mL. At 5 U/mL was observed a slight inhibition of growth at 72 hr. from start of exposure to the enzyme, as shown in FIG. 2.

MGL-BL929 Produces Long Duration Depletion of L-Methionine and L-Homocysteine in the Supernatant of Human Tumor Cell Cultures.

Exposure to MGL-BL929 decreased rapidly the levels of methionine in the supernatant of all four cell lines studied, and the effect was augmented with increasing concentrations of the enzyme. The degree of methionine depletion achieved with a given concentration of MGL-BL929 was maintained during all the duration of the experiment, as shown in FIGS. 3A-B and 4A-B.

Figures are similar with L-homocysteine, the endogenous precursor of methionine, which originates from cells during their growth. As for L-methionine, L-homocysteine concentration in the supernatant of cell cultures strongly decreases under exposure to MGL-BL929, and the effect was augmented with increasing concentrations of the enzyme.

The Recombinant MGL-BL929 is Stable Under Tumor Cell Culture Conditions for Long Periods of Time.

The stability of the recombinant MGL-BL929 was studied in the supernatant of HT29 cell culture. Control is the purified recombinant MGL-BL929 at 1 U/mL in fresh DMEM medium. The supernatant of HT29 cells exposed to MGL-BL929 at 1 U/mL at t0 were harvested at 24 hr., 48 hr., 72 hr., and 96 hr. from start of the experiment.

Western Blot analysis performed with a polyclonal rabbit anti purified MGL-BL929 serum could not show any detectable protein alteration during 4 days under cell culture conditions. This finding, together with the persistent L-methionine depletion for the same duration after a single exposure to the enzyme, indicates that MGL-BL929 is stable for long periods of time under these conditions.

The Recombinant MGL-BL929 is Stable in Human Serum in vitro for Long Periods of Time.

The stability of the recombinant MGL-BL929 was also studied in human serum in vitro by incubation of the serum with various amounts of the enzyme. As for the supernatant of tumor cell cultures, Western Blot analysis did not reveal any protein changes during 72 hr. from start of the incubation with the enzyme.

The inventors produced and purified one batch of 1.2 g of recombinant MGL-BL929 with a protein purity of 94% and low endotoxin levels (31 EU/mL). MGL-BL929 produced possesses high levels of L-methionine γ-lyase, and L-homocysteinase activity. The enzyme (a) depletes methionine and homocysteine from tumor-cell culture media for long periods, (b) is stable under tumor cell culture conditions, and in human serum in vitro, (c) possesses high cytotoxic activity against various human tumor cells growing in culture, (d) does not affect growth of normal cells at concentrations that are highly cytotoxic for cancer cells, (d) potentiate (modulate) the cytotoxic activity of cytostatic agents, and (d) circumvent prior cell resistance to cytostatics. Thus, the use of MGL-BL929 which presents methionine gamma-lyase and homocysteinase activity is a selective original approach to decrease tumor cell growth, potentiate the cytotoxic activity of cytostatic agents and circumvent prior cell resistance to cytostatics in cancer treatment.

```
                                                               SEQ ID NO: 1
     MTSLHPETLM VHGGMKGLTE AGVHVPAIDL STTNPVNDVA TGGDSYEWLA TGHTLKDGDS        60

AVYQRLWQPG VARFETALAG LEHAEEAVAF ATGMAAMTAA LLAAVSAGTP HIVAVRPLYG       120

GSDHLLETGL LGTTVTWAKE ADIASAIQDD TGLVIVETPA NPSLDLVDLD SVVSAAGNVP       180

VLVDNTFCTP VLQQPISHGA ALVLHSATKY LGGHGDAMGG IIATNADWAM RLRQVRAITG       240

ALLHPMGAYL LHRGLRTLAV RMRAAQTTAG ELAERLDAHP AISVVHYPGL KGQDPRGLLG       300

RQMSGGGAMI AMELAGGFDA ARSFVEHCNL VVHAVSLGGA DTLIQHPASL THRPVAATAK       360

PGDGLIRLSV GLEHVDDLAD DLIAALDASR AAA                                   393

SEQ ID NO: 2
     atgacctcac tgcacccaga aacgctcatg gtccacggcg gaatgaaagg cctcaccgag        60
gcaggagtcc acgtaccggc catcgacctc tcgaccacca acccagtcaa cgatgtcgcc       120
accggcggtg actcctacga atggctcgcc accggccata cgctcaagga cggcgactcg       180
gccgtctacc agcgcctctg gcagcccggt gtcgcacgct tcgagaccgc gctggccggg       240
ctcgaacacg ctgaggaagc agtcgccttc gccacgggca tggccgcaat gactgccgca       300
cttctcgcgg ccgtcagcgc aggaacaccc cacatcgtcg cagtgcgtcc cctctatggc       360
ggaagcgacc acctcctcga aaccggactg ctggggacaa cagtcacatg ggcaaaggaa       420
gccgacatcg cctcggcgat ccaagatgac accggactcg tcattgtcga accccggca       480 aaccccagcc tggaccttgt tgatctcgac agtgtcgtct cagccgccgg caacgtgcct       540
gtgctggtgg acaacacatt ctgcacacct gttctccagc agcccatctc ccacggagcg       600
gccctcgtac tgcacagcgc gacaaaatac ctcggcggtc atggcgatgc catgggcggc       660
atcatcgcca ccaacgccga ctgggcgatg cgcctgcgac aggtccgagc catcacagga       720
gccctgctcc accccatggg cgcgtatctc cttcatcggg gcttgcgcac tctggccgtg       780
cgcatgcgcg cggctcagac caccgccggt gagctcgctg agcgcctgga cgcgcaccct       840
gccatctccg tcgtccacta cccgggactg aaaggccagg acccacgcgg actgctcgga       900
cgccaaatgt ccggtggtgg tgcgatgatc gcgatggagc tcgccggtgg attcgacgcc       960
gcccgcagct tcgtcgaaca ctgcaacctc gtcgtccacg cggtgtccct gggcggcgct      1020
gacactctca tccagcatcc ggcgtcactg actcacaggc cagttgcggc cacggcgaag      1080
cccggcgatg gtctcatccg actctctgtg ggactcgaac acgtcgatga cctggcagac      1140

SEQ ID NO: 3
     atgacctcgc tgcatcccga gacgctgatg gttcatggtg gaatgaaggg tctgaccgaa        60
gctggagttc atgtcccggc aattgatctg agcaccacca atcccgtcaa tgatgtcgca       120
accggtggag attcctatga gtggctggcc accggtcata cgctgaaaga tggtgatagc       180
gcagtttatc agcgtctgtg gcagcctggg gttgctcgtt ttgaaaccgc tctggcaggg       240
```

```
ctggagcatg ctgaagaggc tgttgcattt gcaacgggta tggcagctat gactgcagct      300
ctactggctg cagtttcagc tggaacaccc cacattgttg ctgtaagacc tctgtacggt      360
ggaagcgacc atctgctgga gaccggactg ctgggaacta cggttacttg ggctaaagag      420
gcagatattg caagcgctat tcaagacgat accggactgg ttatagttga aaccccggct      480
aatccttcac tggatctagt cgacctggat tcggttgttt cggcagcagg taatgtaccc      540
gtcctggtcg ataatacttt ttgtactccc gtcctgcagc agcctatttc ccatggagct      600
gcactggtcc tgcattctgc tactaagtat ctgggtgggc acggtgacgc aatgggtggt      660
attattgcaa ccaatgcaga ttgggctatg cgtctgagac aggttagagc aattaccgga      720
gcactgctgc atcctatggg tgcttacctg ctacatcggg gtctccgtac tctggcagta      780
cgtatgcgtg ctgctcagac caccgcaggg gaactggctg aacgtctgga tgctcatccc      840
gcaatttccg ttgttcatta tccgggactg aagggtcagg atccccgtgg actgctggga      900
cgtcaaatgt ccggggggggg ggcgatgatt gctatggaac tggcaggggg ctttgatgca      960
gcacgtagtt ttgttgagca ttgtaatctg gttgttcatg ctgtatccct gggtggtgct     1020
gatactctga ttcagcaccc ggcttcgctg actcataggc ccgtcgcggc cacggcgaaa     1080
cctggtgacg ggctgattag actgtcggta ggactggagc atgttgacga tctggctgat     1140
```

REFERENCES

Throughout this application, various references describe the state of the art to which this invention pertains. The disclosures of these references are hereby incorporated by reference into the present disclosure.

1. Abuchowski A, van Es T, Palczuk N C, Davis F F. Alteration of immunological properties of bovine serum albumin by covalent attachment of polyethylene glycol. J Biol Chem. 1977 Jun. 10; 252(11):3578-81.
2. Amarita F, Yvon M, Nardi M, Chambellon E, Delettre J, Bonnarme P. Identification and Functional Analysis of the Gene Encoding Methionine-γ-Lyase in Brevibacterium linens. Applied and Environmental Microbiology, 2004, 70: 7348-7354.
3. Chapman A P. PEGylated antibodies and antibody fragments for improved therapy: a review. Adv Drug Deliv Rev. 2002 Jun. 17; 54(4):531-45.
4. Cunningham-Rundles C, Zhuo Z, Griffith B, Keenan J. Biological activities of polyethylene-glycol immunoglobulin conjugates. Resistance to enzymatic degradation. J Immunol Methods. 1992 Aug. 10; 152(2):177-90.
5. Forquin-Gomez M. P., Hebert A, Roux A, Aubert J., Proux C., Heilier J. F., Landaud S., Junot C., Bonnarme P., Martin-Verstraete I. Global regulation of the response to sulfur availability in the cheese-related bacterium Brevibacterium aurantiacum. Appl. Environ. Microbiol. 2011, 77:1449-1459.
6. Monfardini C, Schiavon O, Caliceti P, Morpurgo M, Harris J M, Veronese F M. A branched monomethoxypoly(ethylene glycol) for protein modification. Bioconjug Chem. 1995 January-February; 6(1):62-9.
7. Machover D, Zittoun J, Broet P, Metzger G, Orrico M, Goldschmidt E, Schilf A, Tonetti C, Tan Y, Delmas-Marsalet B, Luccioni C, Falissard B, Hoffman R. Cytotoxic synergism of methioninase in combination with 5-fluorouracil and folinic acid. Biochemical Pharmacology 2001, 61: 867-876.
8. Machover D, Zittoun J, Saffroy R, Broet P, Giraudier S, Magnaldo T, Goldschmidt E, Debuire B, Orrico M, Tan Y, Mishal Z, Chevallier O, Tonetti C, Jouault H, Ulusakarya A, Tanguy M-L, Metzger G, Hoffman R M. Treatment of cancer cells with methioninase produces DNA hypomethylation and increases DNA synthesis. Cancer Research 2002, 62: 4685-4689.
9. Soda, K. A spectrophotometric micro-determination of keto acids with 3-methyl 2-benzothiazolone hydrazone. Agric Biol Chem, 1967, 31: 1054-1060.
10. Gavrish E. Yu., V. I. Krauzova, N. V. Potekhina, S. G. Karasev, E. G. Plotnikova, O. V. Altyntseva, L. A. Korosteleva, L. I. Evtushenko. 2004. Three New Species of Brevibacteria, Brevibacterium antiquum sp. nov., Brevibacterium aurantiacum sp. nov., and Brevibacterium permense sp. nov. Microbiology 73(no2): 176-183.

The invention claimed is:

1. A vector comprising a nucleic acid encoding a polypeptide comprising an amino acid sequence as set forth by SEQ ID NO: 1 or a functionally-conservative variant thereof.

2. The vector of claim 1, wherein the nucleic acid encoding for a polypeptide is selected from the group consisting of SEQ ID NO: 2 and SEQ ID NO: 3.

3. A nucleic acid encoding a recombinant polypeptide comprising an amino acid sequence as set forth by SEQ ID NO: 1 or a functionally-conservative variant thereof.

4. The nucleic acid according to claim 3 comprising a sequence as set forth by SEQ ID NO: 2.

5. The nucleic acid according to claim 3 comprising a sequence as set forth by SEQ ID NO: 3.

6. A host cell, which has been transformed by
a nucleic acid encoding a recombinant polypeptide comprising an amino acid sequence as set forth by SEQ ID NO: 1 or a functionally-conservative variant thereof and/or
a vector comprising a nucleic acid encoding a polypeptide comprising an amino acid sequence as set forth by SEQ ID NO: 1 or a functionally-conservative variant thereof.

7. A pharmaceutical composition comprising
i) a recombinant polypeptide comprising an amino acid sequence as set forth by SEQ ID NO: 1 or a functionally-conservative variant thereof, or a nucleic acid encoding a polypeptide comprising an amino acid sequence as set forth by SEQ ID NO: 1 or a functionally-conservative variant thereof, or a vector comprising said nucleic acid, and
ii) a pharmaceutically acceptable carrier.

8. The pharmaceutical composition according to claim 7 comprising one or more enzyme cofactors.

9. The pharmaceutical composition according to claim 7 comprising one or more chemotherapeutic or radiotherapeutic agents.

10. A recombinant polypeptide comprising an amino acid sequence as set forth by SEQ ID NO: 1 or a functionally-conservative variant thereof contained in a vector.

11. A polypeptide comprising an amino acid sequence as set forth by SEQ ID NO: 1 or a functionally-conservative variant thereof which is covalently conjugated with at least one polyethylene glycol group.

12. A polypeptide comprising an amino acid sequence as set forth by SEQ ID NO: 1 or a functionally-conservative variant thereof which is covalently coupled to a tumor targeting agent.

13. A method of producing a polypeptide comprising an amino acid sequence as set forth by SEQ ID NO: 1, which method comprises the steps of:
i) culturing a host cell transformed by
  a) a nucleic acid encoding a recombinant polypeptide comprising an amino acid sequence as set forth by SEQ ID NO: 1 or a functionally-conservative variant thereof,
and/or
  b) a vector comprising a nucleic acid encoding a polypeptide comprising an amino acid sequence as set forth by SEQ ID NO: 1 or a functionally-conservative variant thereof,
under condition suitable to allow expression of said polypeptide; and
(ii) recovering the expressed polypeptide.

14. A method for treating a cancer in a subject of need thereof comprising the step of administering to said subject a polypeptide comprising an amino acid sequence as set forth by SEQ ID NO: 1 or a functionally-conservative variant thereof.

15. A method for treating a cancer in a subject of need thereof comprising the step of administering to said subject a nucleic acid encoding a polypeptide comprising an amino acid sequence as set forth by SEQ ID NO: 1 or a functionally-conservative variant thereof, or a vector comprising said nucleic acid.

16. A method for treating a cancer in a subject of need thereof comprising the step of administering to said subject a combination of
i) a polypeptide comprising an amino acid sequence as set forth by SEQ ID NO: 1 or a functionally-conservative variant thereof, or a nucleic acid encoding a polypeptide comprising an amino acid sequence as set forth by SEQ ID NO: 1 or a functionally-conservative variant thereof, or a vector comprising said nucleic acid, and
ii) one or more agents selected from the group consisting of: one or more enzyme cofactors and one or more chemotherapeutic or radiotherapeutic agents.

\* \* \* \* \*

SEQUENCE LISTING

<160> NUMBER OF SEQ ID NOS: 3

<210> SEQ ID NO 1
<211> LENGTH: 393
<212> TYPE: PRT
<213> ORGANISM: Brevibacterium linens

<400> SEQUENCE: 1

Met Thr Ser Leu His Pro Glu Thr Leu Met Val His Gly Gly Met Lys

```
            1               5              10              15
          Gly Leu Thr Glu Ala Gly Val His Val Pro Ala Ile Asp Leu Ser Thr
                          20              25              30
          Thr Asn Pro Val Asn Asp Val Ala Thr Gly Gly Asp Ser Tyr Glu Trp
                          35              40              45
          Leu Ala Thr Gly His Thr Leu Lys Asp Gly Asp Ser Ala Val Tyr Gln
           50              55              60
          Arg Leu Trp Gln Pro Gly Val Ala Arg Phe Glu Thr Ala Leu Ala Gly
           65              70              75              80
          Leu Glu His Ala Glu Glu Ala Val Ala Phe Ala Thr Gly Met Ala Ala
                          85              90              95
          Met Thr Ala Ala Leu Leu Ala Ala Val Ser Ala Gly Thr Pro His Ile
                         100             105             110
          Val Ala Val Arg Pro Leu Tyr Gly Gly Ser Asp His Leu Leu Glu Thr
                         115             120             125
          Gly Leu Leu Gly Thr Thr Val Thr Trp Ala Lys Glu Ala Asp Ile Ala
                         130             135             140
          Ser Ala Ile Gln Asp Asp Thr Gly Leu Val Ile Val Glu Thr Pro Ala
          145             150             155             160
          Asn Pro Ser Leu Asp Leu Val Asp Leu Asp Ser Val Val Ser Ala Ala
                         165             170             175
          Gly Asn Val Pro Val Leu Val Asp Asn Thr Phe Cys Thr Pro Val Leu
                         180             185             190
          Gln Gln Pro Ile Ser His Gly Ala Ala Leu Val Leu His Ser Ala Thr
                         195             200             205
          Lys Tyr Leu Gly Gly His Gly Asp Ala Met Gly Gly Ile Ile Ala Thr
                         210             215             220
          Asn Ala Asp Trp Ala Met Arg Leu Arg Gln Val Arg Ala Ile Thr Gly
          225             230             235             240
          Ala Leu Leu His Pro Met Gly Ala Tyr Leu Leu His Arg Gly Leu Arg
                         245             250             255
          Thr Leu Ala Val Arg Met Arg Ala Ala Gln Thr Thr Ala Gly Glu Leu
                         260             265             270
          Ala Glu Arg Leu Asp Ala His Pro Ala Ile Ser Val Val His Tyr Pro
                         275             280             285
          Gly Leu Lys Gly Gln Asp Pro Arg Gly Leu Leu Gly Arg Gln Met Ser
                         290             295             300
          Gly Gly Gly Ala Met Ile Ala Met Glu Leu Ala Gly Phe Asp Ala
          305             310             315             320
          Ala Arg Ser Phe Val Glu His Cys Asn Leu Val Val His Ala Val Ser
                         325             330             335
          Leu Gly Gly Ala Asp Thr Leu Ile Gln His Pro Ala Ser Leu Thr His
                         340             345             350
          Arg Pro Val Ala Ala Thr Ala Lys Pro Gly Asp Gly Leu Ile Arg Leu
                         355             360             365
          Ser Val Gly Leu Glu His Val Asp Asp Leu Ala Asp Asp Leu Ile Ala
                         370             375             380
          Ala Leu Asp Ala Ser Arg Ala Ala Ala
          385             390

<210> SEQ ID NO 2
<211> LENGTH: 1182
<212> TYPE: DNA
<213> ORGANISM: Brevibacterium linens
```

<400> SEQUENCE: 2

```
atgacctcac tgcacccaga acgctcatg gtccacggcg aatgaaagg cctcaccgag    60
gcaggagtcc acgtaccggc catcgacctc tcgaccacca acccagtcaa cgatgtcgcc   120
accggcggtg actcctacga atggctcgcc accggccata cgctcaagga cggcgactcg   180
gccgtctacc agcgcctctg cagcccggt gtcgcacgct cgagaccgc gctggccggg   240
ctcgaacacg ctgaggaagc agtcgccttc gccacgggca tggccgcaat gactgccgca   300
cttctcgcgg ccgtcagcgc aggaacaccc cacatcgtcg cagtgcgtcc cctctatggc   360
ggaagcgacc acctcctcga aaccggactg ctggggacaa cagtcacatg ggcaaaggaa   420
gccgacatcg cctcggcgat ccaagatgac accggactcg tcattgtcga accccggca    480
aaccccagcc tggaccttgt tgatctcgac agtgtcgtct cagccgccgg caacgtgcct   540
gtgctggtgg acaacacatt ctgcacacct gttctccagc agcccatctc ccacggagcg   600
gccctcgtac tgcacagcgc gacaaaatac ctcggcggtc atggcgatgc catgggcggc   660
atcatcgcca ccaacgccga ctgggcgatg cgcctgcgac aggtccgagc catcacagga   720
gccctgctcc accccatggg cgcgtatctc cttcatcggg gcttgcgcac tctggccgtg   780
cgcatgcgcg cggctcagac caccgccggt gagctcgctg agcgcctgga cgcgcaccct   840
gccatctccg tcgtccacta cccgggactg aaaggccagg acccacgcgg actgctcgga   900
cgccaaatgt ccggtggtgg tgcgatgatc gcgatggagc tcgccggtgg attcgacgcc   960
gcccgcagct tcgtcgaaca ctgcaacctc gtcgtccacg cggtgtccct gggcggcgct  1020
gacactctca tccagcatcc ggcgtcactg actcacaggc cagttgcggc cacggcgaag  1080
cccggcgatg gtctcatccg actctctgtg ggactcgaac acgtcgatga cctggcagac  1140
gatctcatcg ctgccctcga cgcgagtcgg gccgctgcct ga                    1182
```

<210> SEQ ID NO 3
<211> LENGTH: 1182
<212> TYPE: DNA
<213> ORGANISM: Brevibacterium linens

<400> SEQUENCE: 3

```
atgacctcgc tgcatcccga cgcgctgatg gttcatggtg aatgaaggg tctgaccgaa    60
gctggagttc atgtcccggc aattgatctg agcaccacca atcccgtcaa tgatgtcgca   120
accggtggag attcctatga gtggctggcc accggtcata cgctgaaaga tggtgatagc   180
gcagtttatc agcgtctgtg gcagcctggg gttgctcgtt ttgaaaccgc tctggcaggg   240
ctggagcatg ctgaagaggc tgttgcattt gcaacgggta tggcagctat gactgcagct   300
ctactggctg cagtttcagc tggaacaccc cacattgttg ctgtaagacc tctgtacggt   360
ggaagcgacc atctgctgga gaccggactg ctgggaacta cggttacttg gctaaagag    420
gcagatattg caagcgctat tcaagacgat accggactgg ttatagttga accccggct    480
aatccttcac tggatctagt cgacctggat tcggttgttt cggcagcagg taatgtaccc   540
gtcctggtcg ataatacttt ttgtactccc gtcctgcagc agcctatttc ccatggagct   600
gcactggtcc tgcattctgc tactaagtat ctgggtgggc acggtgacgc aatgggtggt   660
attattgcaa ccaatgcaga ttgggctatg cgtctgagac aggttagagc aattaccgga   720
gcactgctgc atcctatggg tgcttacctg ctacatcggg gtctccgtac tctggcagta   780
cgtatgcgtg ctgctcagac caccgcaggg gaactggctg aacgtctgga tgctcatccc   840
```

-continued

```
gcaatttccg ttgttcatta tccgggactg aagggtcagg atccccgtgg actgctggga    900
cgtcaaatgt ccggggggg ggcgatgatt gctatggaac tggcaggggg ctttgatgca    960
gcacgtagtt ttgttgagca ttgtaatctg gttgttcatg ctgtatccct gggtggtgct   1020
gatactctga ttcagcaccc ggcttcgctg actcataggc ccgtcgcggc cacggcgaaa   1080
cctggtgacg ggctgattag actgtcggta ggactggagc atgttgacga tctggctgat   1140
gacctgattg ctgcactgga tgcttcgcgg gcagctgcat aa                      1182
```